(12) United States Patent
Yamashita et al.

(10) Patent No.: US 12,390,103 B2
(45) Date of Patent: Aug. 19, 2025

(54) ESTIMATION DEVICE, ESTIMATION METHOD, AND ESTIMATION PROGRAM

(71) Applicant: Nippon Telegraph and Telephone Corporation, Tokyo (JP)

(72) Inventors: Jumpei Yamashita, Musashino (JP); Hidetaka Koya, Musashino (JP); Akira Kataoka, Musashino (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 354 days.

(21) Appl. No.: 18/037,596

(22) PCT Filed: Nov. 19, 2020

(86) PCT No.: PCT/JP2020/043246
§ 371 (c)(1),
(2) Date: May 18, 2023

(87) PCT Pub. No.: WO2022/107288
PCT Pub. Date: May 27, 2022

(65) Prior Publication Data
US 2023/0404393 A1 Dec. 21, 2023

(51) Int. Cl.
*A61B 3/11* (2006.01)
(52) U.S. Cl.
CPC .................. *A61B 3/112* (2013.01)
(58) Field of Classification Search
CPC ....................................................... A61B 3/112
USPC ....................................................... 351/205
See application file for complete search history.

(56) References Cited

U.S. PATENT DOCUMENTS

| 8,136,944 B2 * | 3/2012 | De Lemos | G06V 40/19 |
| | | | 382/103 |
| 2004/0233061 A1 * | 11/2004 | Johns | G06V 40/19 |
| | | | 340/575 |
| 2006/0202841 A1 * | 9/2006 | Johns | G06V 40/19 |
| | | | 340/575 |
| 2020/0187840 A1 * | 6/2020 | Yamaji | G08G 1/16 |
| 2021/0282639 A1 * | 9/2021 | Yokoyama | G02B 27/02 |

OTHER PUBLICATIONS

[No Author Listed] [online], "Pupillographic Assessment of Sleepiness in Sleep-deprived Healthy Subjects," Sleep, retrieved on Nov. 2, 2020, retrieved from URL <https://pubmed.ncbi.nlm.nih.gov/9595604/>, 21:258-265.

(Continued)

*Primary Examiner* — Sharrief I Broome
(74) *Attorney, Agent, or Firm* — Fish & Richardson P.C.

(57) ABSTRACT

An estimation device includes processing circuitry configured to acquire a pupil diameter of a subject whose work performance is to be estimated at a time of work and a luminance of a gaze target of the subject, calculate a variation amount of the pupil diameter of the subject from time-series data of the pupil diameter of the subject, determine whether or not the luminance of the gaze target of the subject is equal to or higher than a predetermined value, and determine that a correlation between a magnitude of the variation amount of the pupil diameter of the subject and a deterioration in the work performance of the subject is low in a case where it is determined that the luminance of the gaze target of the subject is equal to or higher than a predetermined threshold.

9 Claims, 7 Drawing Sheets

(56) References Cited

OTHER PUBLICATIONS

Binda et al., "Attention to Bright Surfaces Enhances the Pupillary Light Reflex," Journal of Neuroscience, retrieved on Nov. 2, 2020, retrieved from URL <https://www.ncbi.nlm.nih.gov/pmc/articles/PMC6619119/>, 33(5):2199-2204, 11 pages.

* cited by examiner

ESTIMATION DEVICE, ESTIMATION METHOD, AND ESTIMATION PROGRAM

CROSS-REFERENCE TO RELATED APPLICATIONS

This application is a National Stage application under 35 U.S.C. § 371 of International Application No. PCT/JP2020/043246, having an International Filing Date of Nov. 19, 2020, the disclosure of which is considered part of the disclosure of this application, and is incorporated by reference in its entirety into this application.

TECHNICAL FIELD

The present invention relates to an estimation device, an estimation method, and an estimation program for estimating a performance of a worker performing a task.

BACKGROUND ART

When a human performs work (performs a cognitive task) while the human is visually checking something, a performance of the human performing the task is sometimes good and sometimes bad. Here, as a method of estimating a performance of a worker performing a task, there is a method of using a variation amount of a pupil diameter of the worker.

When a performance of a worker performing a task (hereinafter, appropriately referred to as a "task performance") is estimated by the method using a variation amount of a pupil diameter of the worker, the worker is placed in darkness for a predetermined time, and the variation amount of the pupil diameter of the worker is measured. Here, it is known that a large wave appears in the variation amount of the pupil diameter of the worker in a case where the task performance of the worker is deteriorated such as when the worker is hindered from sleeping for a long time, for example (see Non Patent Literature 1).

Therefore, it is estimated that the task performance of the worker is low in a case where the variation amount of the pupil diameter of the worker in darkness is large, and the task performance of the worker is high in a case where the variation amount of the pupil diameter is small. Note that the variation in the pupil diameter that is observed in darkness, which changes reflecting the deterioration in the task performance, is hereinafter referred to as "variation in the pupil diameter correlated with the deterioration in the performance".

The reason why the worker is placed in darkness for the predetermined time when the task performance of the worker is estimated is that, when the brightness of the position at which the worker is gazing changes, a temporary variation occurs in the pupil diameter due to light adaptation or dark adaptation. In addition, even if the brightness of the position at which the worker is gazing does not change, the pupil diameter varies if the position at which the worker is gazing is bright. Note that the variation in the pupil diameter caused by light is hereinafter referred to as "light-dependent variation in the pupil diameter".

CITATION LIST

Non Patent Literature

Non Patent Literature 1: Pupillographic Assessment of Sleepiness in Sleep-deprived Healthy Subjects. Sleep, 21, 258-265, [Searched on Nov. 2, 2020], Internet <URL: pubmed.ncbi.nlm.nih.gov/9595604/>

Non Patent Literature 2: Binda, P., Pereverzeva, M., & Murray, S. O. (2013). Attention to Bright Surfaces Enhances the Pupillary Light Reflex. Journal of Neuroscience, 33 (5), 2199-2204. doi:10.1523/jneurosci.3440-12.2013 [Searched on Nov. 2, 2020], Internet <URL: www.ncbi.nlm.nih.gov/pmc/articles/PMC6619119/>

SUMMARY OF INVENTION

Technical Problem

However, in the conventional technique, it is necessary to place a worker in darkness for a predetermined time in order to estimate a task performance of the worker. For this reason, there is a problem that it is not possible to estimate a task performance of a worker performing a task.

Therefore, an object of the present invention is to solve the problem and to estimate a task performance of a worker performing a task.

Solution to Problem

In order to achieve the object, the estimation device includes: processing circuitry configured to: acquire a pupil diameter of a subject whose work performance is to be estimated at a time of work and a luminance of a gaze target of the subject; calculate a variation amount of the pupil diameter of the subject from time-series data of the pupil diameter of the subject; determine whether or not the luminance of the gaze target of the subject is equal to or higher than a predetermined value; and determine that a correlation between a magnitude of the variation amount of the pupil diameter of the subject and a deterioration in the work performance of the subject is low in a case where it is determined that the luminance of the gaze target of the subject is equal to or higher than a predetermined threshold, determine that the correlation between the magnitude of the variation amount of the pupil diameter of the subject and the deterioration in the work performance of the subject is high in a case where it is determined that the luminance of the gaze target of the subject is lower than the predetermined threshold, and estimate the work performance of the subject based on a result of the determination and the variation amount of the pupil diameter of the subject.

Advantageous Effects of Invention

According to the present invention, it is possible to estimate a task performance of a worker performing a task.

DESCRIPTION OF EMBODIMENTS

Figure 1:
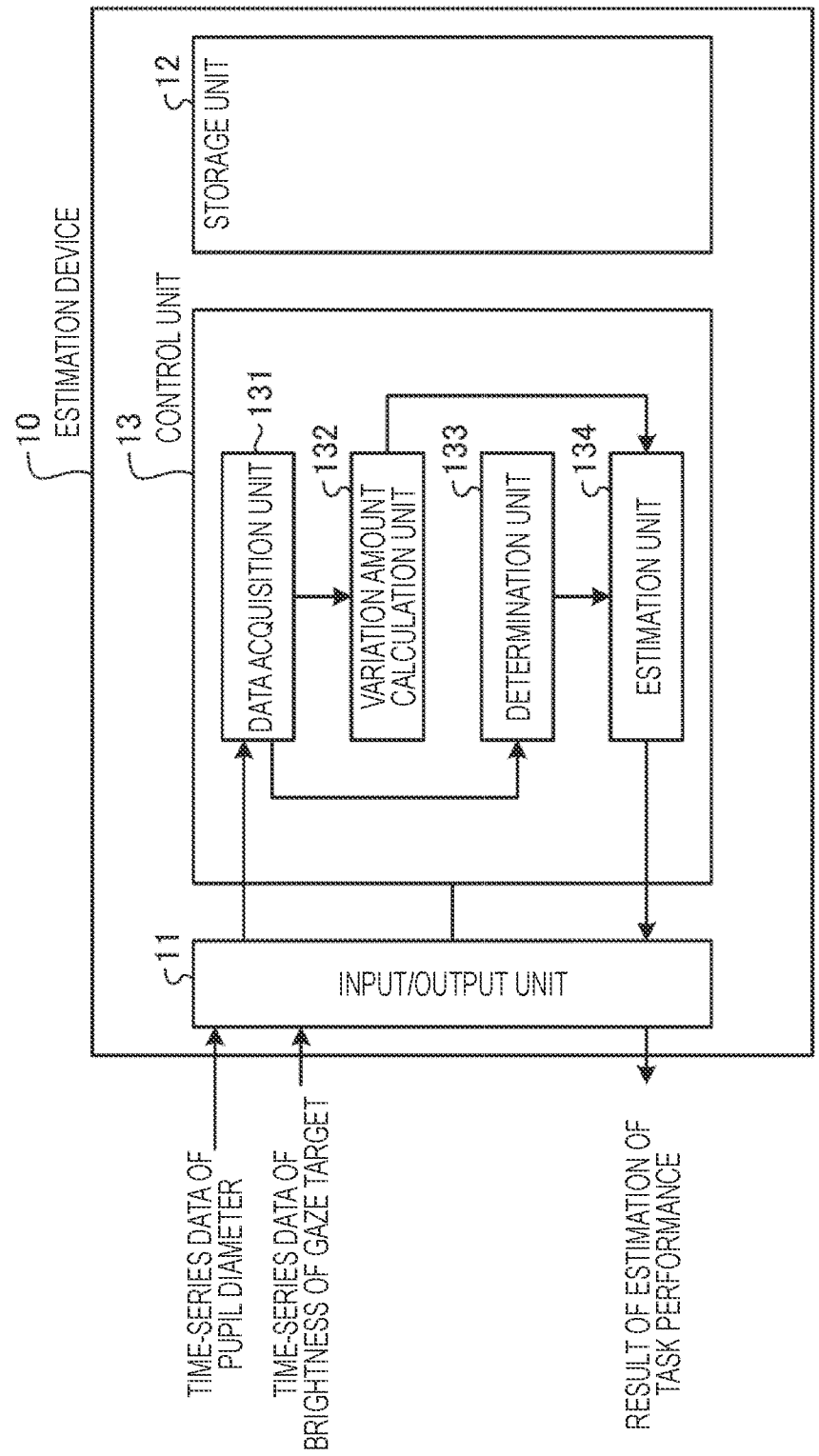
FIG. 1 is a diagram illustrating a configuration example of an estimation device.

Hereinafter, modes (embodiments) for carrying out the present invention will be described with reference to the drawings. The present invention is not limited to the embodiments described below.

[Outline] First, an operation outline of an estimation device of the present embodiment will be described. The estimation device estimates a work performance (task performance) of a worker executing a task.

First, the estimation device acquires a variation amount of a pupil diameter of the worker (the subject whose task performance is to be estimated) executing the task and the brightness of the position at which the subject is supposed to be gazing (gaze target). Here, the estimation device estimates the task performance in a mode corresponding to a case where the brightness of the gaze target is lower than a predetermined value or in a mode corresponding to a case where the brightness of the gaze target is equal to or higher than the predetermined value.

For example, in the case where the brightness of the gaze target of the subject is lower than the predetermined value, it is considered that the variation in the pupil diameter of the subject is less related to the "light-dependent variation in the pupil diameter" and is more related to the "variation in the pupil diameter correlated with the deterioration in the task performance".

Therefore, in the case where the brightness of the gaze target of the subject is lower than the predetermined value, the estimation device estimates that the correlation between the magnitude of the variation amount of the pupil diameter of the subject and the deterioration in the task performance of the subject is high. For example, in the case where the brightness of the gaze target of the subject is lower than the predetermined value, the estimation device estimates that the task performance of the subject is low when the variation amount of the pupil diameter of the subject is large, and the task performance of the subject is high when the variation amount of the pupil diameter of the subject is small.

On the other hand, in the case where the brightness of the gaze target of the subject is equal to or higher than the predetermined value, it is considered that the variation in the pupil diameter of the subject is more related to the "light-dependent variation in the pupil diameter" and is not less related to the "variation in the pupil diameter correlated with the deterioration in the task performance".

Therefore, in the case where the brightness of the gaze target of the subject is equal to or higher than the predetermined value, the estimation device estimates that the correlation between the magnitude of the variation amount of the pupil diameter of the subject and the deterioration in the task performance of the subject is low.

Here, the variation in the pupil diameter caused by the brightness of the gaze target increases when the subject pays attention to the gaze target. In addition, in the case where the subject pays attention to the gaze target, it is considered that the task performance is improved. Therefore, for example, in the case where the brightness of the gaze target of the subject is equal to or higher than the predetermined value, the estimation device estimates that the task performance of the subject is high when the variation amount of the pupil diameter of the subject is large, and the task performance of the subject is low when the variation amount of the pupil diameter of the subject is small.

In this way, the estimation device can estimate the task performance of the subject performing the task.

Note that the description will be made about the reason why it can be estimated that, in the case where the gaze target of the subject is bright, the task performance is high when the variation amount of the pupil diameter of the subject is large, and the task performance is low when the variation amount of the pupil diameter of the subject is small.

Premise Regarding "Light-Dependent Variation in Pupil Diameter"

It is known that, for example, in a case where the luminance of the gaze target of the subject changes, the variation in the pupil diameter caused by the luminance change of the gaze target is larger when the subject pays attention to (properly looks at) the gaze target than when the subject looks at the gaze target aimlessly although the line of sight of the subject is directed to the gaze target (see Non Patent Literature 2). Alternatively, simply, in a case where the line of sight is directed to the gaze target of the subject, the variation in the pupil diameter caused by the luminance change is larger than in a case where even the line of sight is not directed to the gaze target.

Analysis Regarding Task Performance Estimation Scene and Reason why Task Performance Estimation is Possible It is considered that processing on visual information displayed on a monitor screen is most important in the task performed by the subject except for a case where the task performed by the subject is a telephone response or the like. Therefore, it is considered that it is important for the estimation of the task performance that the subject pays attention (the line of sight of the subject is directed) to the monitor screen. For example, in the case where the subject properly pays attention to the monitor screen, the variation amount of the pupil diameter caused by the change in the brightness (for example, luminance) of the monitor screen is large according to the above premise, and thus the task performance can be estimated.

[Configuration example] Next, a configuration example of an estimation device 10 will be described with reference to FIG. 1. The estimation device 10 includes an input/output unit 11, a storage unit 12, and a control unit 13.

The input/output unit 11 manages input and output of various types of data, and receives input of, for example, time-series data of a pupil diameter of a subject performing a task, who is a person whose task performance is to be estimated, time-series data of the brightness (for example, luminance) of a gaze target of the subject, and the like.

Note that the pupil diameter of the subject is acquired by, for example, an optical device using an infrared camera or a visible light camera. Furthermore, the brightness of the gaze position of the subject may be acquired by, for example, the above optical device, or in a case where the task performed by the subject is visual display terminal (VDT) work, a rough brightness may be estimated from an approximate color of a screen displayed on a display.

In addition, the input/output unit 11 outputs a result of estimation of the task performance of the subject obtained by the control unit 13. The storage unit 12 stores various types of data to be referred to when the control unit 13 executes processing.

The control unit 13 controls the entire estimation device 10. The control unit 13 includes, for example, a data acquisition unit 131, a variation amount calculation unit 132, a determination unit 133, and an estimation unit 134.

The data acquisition unit 131 acquires the time-series data of the pupil diameter of the subject, the time-series data of the brightness of the gaze target of the subject, and the like via the input/output unit 11.

The variation amount calculation unit 132 calculates a variation amount of the pupil diameter of the subject based on the time-series data of the pupil diameter of the subject acquired by the data acquisition unit 131.

The determination unit 133 determines whether or not the brightness (for example, luminance) of the gaze target of the subject acquired by the data acquisition unit 131 is equal to or higher than a predetermined value.

The estimation unit 134 estimates the task performance of the subject by using the determination result of the brightness of the gaze target of the subject determined by the determination unit 133 and the variation amount of the pupil diameter of the subject calculated by the variation amount calculation unit 132. The estimation unit 134 then outputs the result of estimation of the task performance of the subject.

For example, in a case where the determination unit 133 determines that the brightness of the gaze target of the subject is equal to or higher than a predetermined threshold, the estimation unit 134 determines that the correlation between the magnitude of the variation amount of the pupil diameter of the subject and the deterioration in the task performance of the subject is low.

For example, the estimation unit 134 determines that the magnitude of the variation amount of the pupil diameter of the subject and the level of the task performance of the subject have a positive correlation, and estimates that the larger the variation amount of the pupil diameter of the subject, the higher the task performance of the subject. Furthermore, the estimation unit 134 estimates that the smaller the variation amount of the pupil diameter of the subject, the lower the task performance of the subject.

On the other hand, in a case where the determination unit 133 determines that the brightness of the gaze target of the subject is lower than the predetermined threshold, the estimation unit 134 determines that the correlation between the magnitude of the variation in the pupil diameter of the subject and the deterioration in the task performance of the subject is high.

For example, the estimation unit 134 determines that the magnitude of the variation amount of the pupil diameter of the subject and the level of the task performance of the subject have a negative correlation, and estimates that the larger the variation amount of the pupil diameter of the subject, the lower the task performance of the subject. Furthermore, the estimation unit 134 estimates that the smaller the variation amount of the pupil diameter of the subject, the higher the task performance of the subject.

In this way, the estimation device 10 can estimate the task performance of the subject performing the task.

Figure 2:
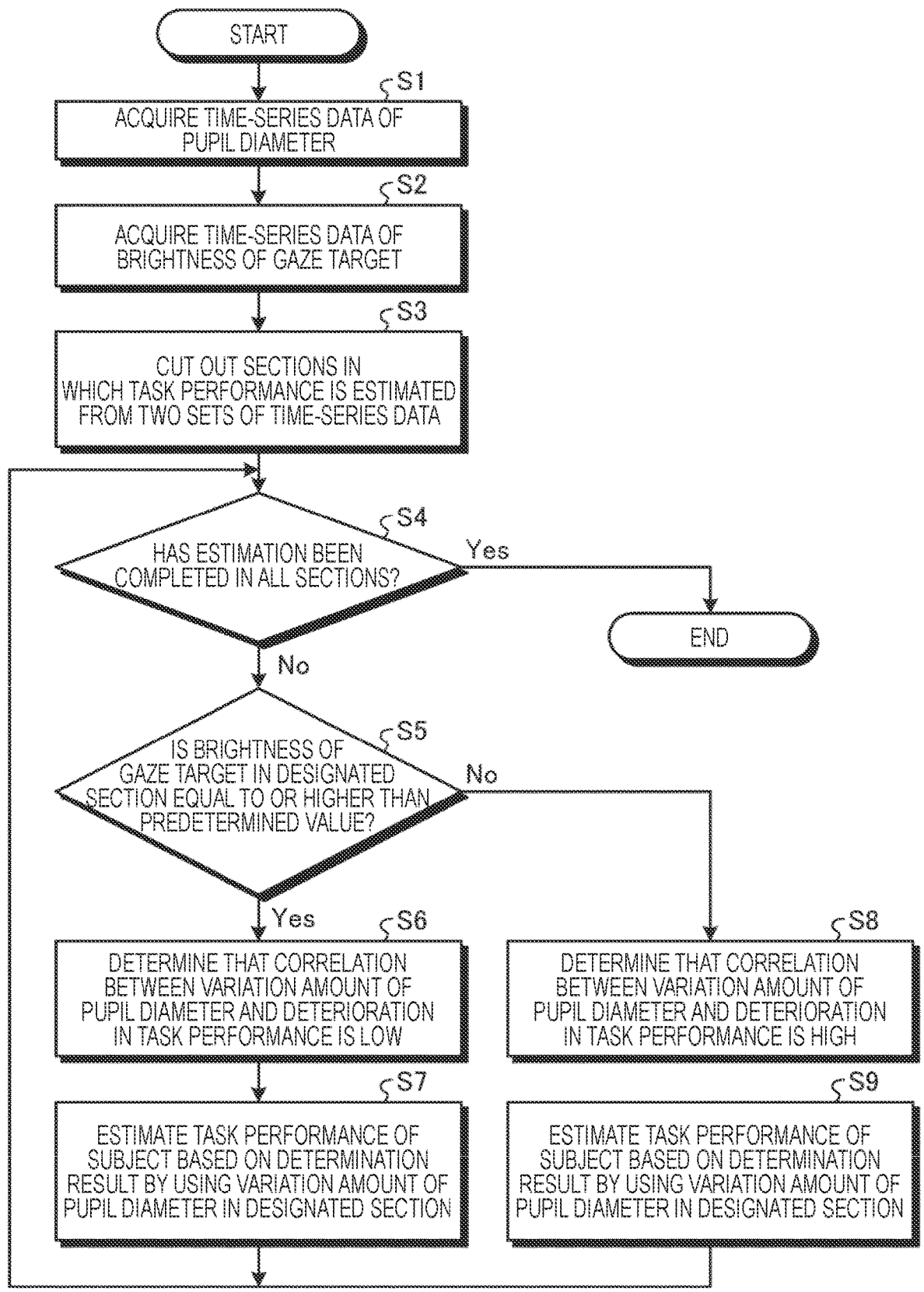
FIG. 2 is a flowchart illustrating an example of a processing procedure of the estimation device of FIG. 1.

[Example of processing procedure] Next, an example of a processing procedure of the estimation device 10 will be described with reference to FIG. 2. First, the data acquisition unit 131 of the estimation device 10 acquires time-series data of a pupil diameter of a subject (S1). In addition, the data acquisition unit 131 acquires time-series data of the brightness of a gaze target of the subject (S2). The data acquisition unit 131 then cuts out sections in which a task performance is estimated from the two sets of time-series data (the time-series data of the pupil diameter of the subject and the time-series data of the brightness of the gaze target) (S3).

Here, if the estimation of the task performance has been completed in all the sections cut out in S3 (Yes in S4), the processing is ended, and if there is a section in which the estimation has not been completed yet (No in S4), the processing proceeds to S5.

In S5, the determination unit 133 determines whether or not the brightness of the gaze target in a designated section (a section selected from the sections in which the task performance has not been estimated yet) is equal to or higher than a predetermined value. Here, in a case where the determination unit 133 determines that the brightness of the gaze target in the designated section is equal to or higher than the predetermined value (Yes in S5), the estimation unit 134 determines that the correlation between the variation in the pupil diameter of the subject and the deterioration in the task performance is low (S6). Based on the determination result, the estimation unit 134 then estimates the task performance of the subject by using the variation amount of the pupil diameter in the designated section (S7). The processing then returns to S4.

On the other hand, in a case where the determination unit 133 determines that the brightness of the gaze target in the designated section is lower than the predetermined value (No in S5), the estimation unit 134 determines that the correlation between the variation in the pupil diameter of the subject and the deterioration in the task performance is high (S8). Based on the determination result, the estimation unit 134 then estimates the task performance of the subject by using the variation amount of the pupil diameter in the designated section (S9). The processing then returns to S4.

Figure 3:
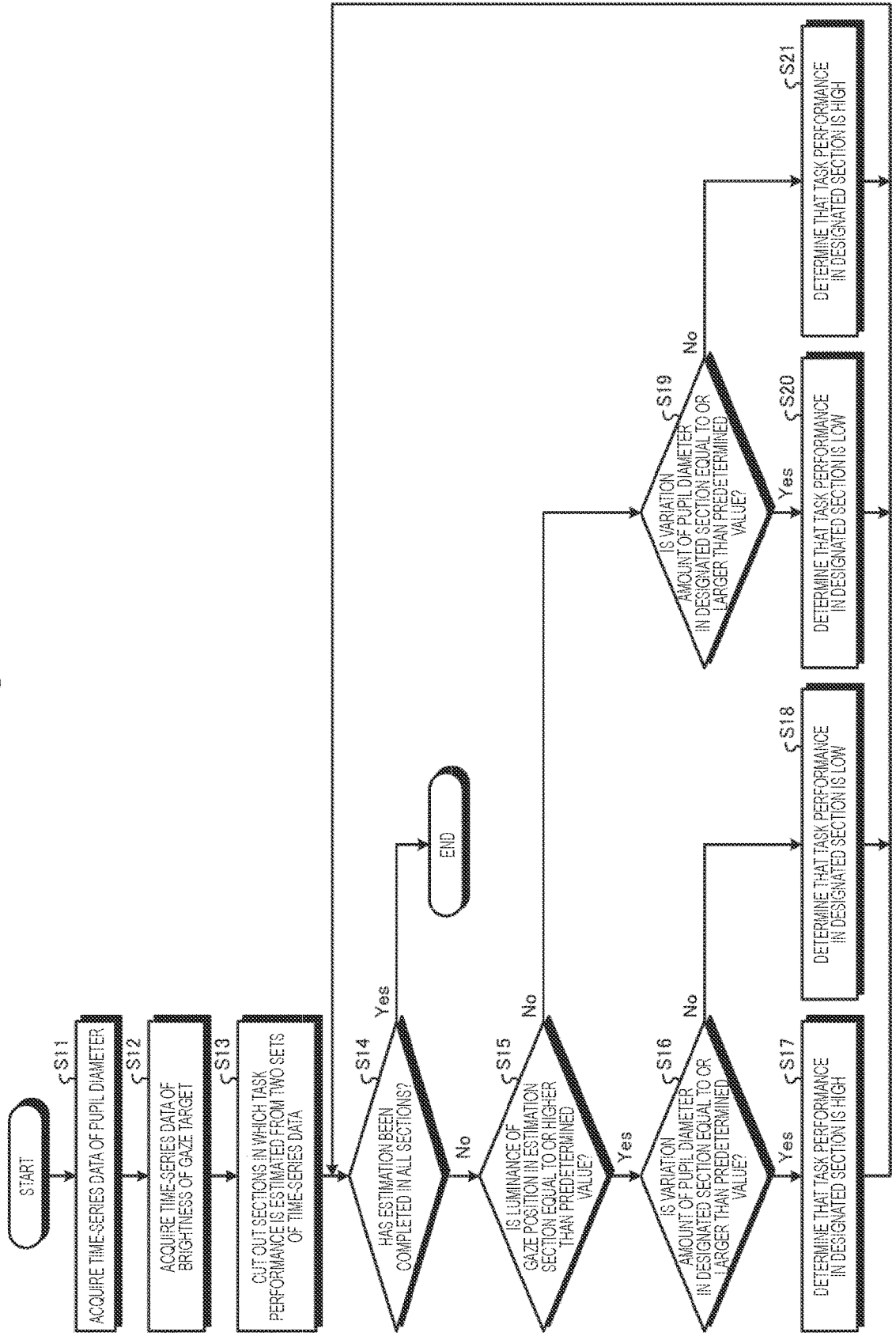
FIG. 3 is a diagram illustrating an example of the processing procedure illustrated in FIG. 2.

Next, an example of the processing procedure of the estimation device 10 illustrated in FIG. 2 will be described with reference to FIG. 3. Since processing from S11 to S14 illustrated in FIG. 3 is similar to the processing from S1 to S4 in FIG. 2, processing from S15 in FIG. 3 will be described.

In S15, the determination unit 133 determines whether or not the luminance of the gaze target in the designated section is equal to or higher than a predetermined value. Here, in a case where the determination unit 133 determines that the luminance of the gaze target in the designated section is equal to or higher than the predetermined value (Yes in S15), and the variation amount of the pupil diameter in the designated section is equal to or larger than a predetermined value (Yes in S16), the estimation unit 134 determines that the task performance in the designated section is high (S17). Thereafter, the processing returns to S14. On the other hand, in a case where the variation amount of the pupil diameter in the designated section is smaller than the predetermined value (No in S16), the estimation unit 134 determines that the task performance in the designated section is low (S18). Thereafter, the processing returns to S14.

Furthermore, in a case where the determination unit 133 determines that the luminance of the gaze target in the designated section is lower than the predetermined value in S15 (No in S15), and the variation amount of the pupil diameter in the designated section is equal to or larger than the predetermined value (Yes in S19), the estimation unit 134 determines that the task performance in the designated section is low (S20). Thereafter, the processing returns to S14. On the other hand, if the variation amount of the pupil diameter in the designated section is smaller than the predetermined value (No in S19), the estimation unit 134 determines that the task performance in the designated section is high (S21). Thereafter, the processing returns to S14.

In this way, the estimation device 10 can estimate the task performance of the worker performing the task.

[Other embodiments] Note that, when calculating the variation amount of the pupil diameter of the subject, the variation amount calculation unit 132 may set, as invalid sections, a section during blinking and sections before and after the blinking in the time-series data of the pupil diameter and exclude the invalid sections.

Figure 4:
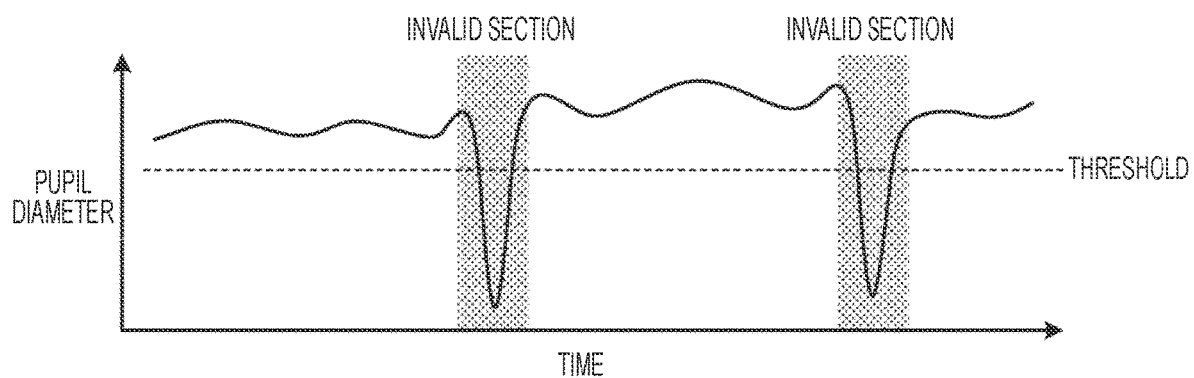
FIG. 4 is a diagram for describing time-series data of a pupil diameter of a subject and an invalid section in the time-series data.

Here, when the variation amount calculation unit 132 detects the occurrence of blinking, in consideration of the nature of a biological system that controls the pupil diameter, an algorithm may be used in which a case where such a small pupil diameter that cannot be calculated unless the eyelid is closed is measured (a case where the pupil diameter illustrated in FIG. 4 is equal to or smaller than a predetermined threshold) is regarded as the occurrence of blinking.

For example, consider a case where the time-series data of the pupil diameter of the subject indicates values illustrated in FIG. 4. In this case, as illustrated in FIG. 4, the variation amount calculation unit 132 sets, as invalid spaces, a section in which the value of the pupil diameter is equal to or smaller than the predetermined threshold and sections before and after the section. The variation amount calculation unit 132 then excludes the data in the invalid spaces from the time-series data of the pupil diameter of the subject. In this way, the variation amount calculation unit 132 can accurately calculate the variation amount of the pupil diameter of the subject.

Furthermore, when calculating the variation amount of the pupil diameter, the variation amount calculation unit 132 may reduce measurement noise of the pupil diameter by smoothing the time-series data of the pupil diameter in advance using a low-pass filter, a moving average, or the like. As the simplest method of calculating the variation amount of the pupil diameter, there is a method in which the variation amount calculation unit 132 obtains first-order differential values of data in a section in which a task performance is estimated among the time-series data of the pupil diameter, takes absolute values of the values of the obtained time-series data of the variation amount of the pupil diameter, and calculates the average of the obtained absolute values.

Note that the variation amount calculation unit 132 may calculate a value obtained by incorporating a relationship generally seen in biological information as function conversion. For example, the variation amount calculation unit 132 may logarithmically transform the variation amount of the pupil diameter obtained from the time-series data of the pupil diameter.

[Experiment] Hereinafter, a result of an experiment will be described that indicates that the estimation device 10 can estimate a task performance of a subject by using a variation amount of a pupil diameter of the subject executing a task.

[Experimental conditions] In this experiment, task performances of six subjects each performing a task described below were estimated. The task was that each subject continued to gaze at a monitor on which a black background screen was displayed, and pressed a button as quickly as possible when a white circle (target) appeared, and such a trial was repeated 116 times.

In this experiment, since the place at which each subject was gazing (gaze screen) was dark, it can be estimated that the correlation between the magnitude of a variation amount of a pupil diameter of each subject executing the task and the deterioration in a task performance was strong. In other words, in a case where a variation amount of a pupil diameter of a subject executing the task was small, it can be estimated that a task performance of the subject was high.

In this experiment, a time from the start of a trial to the appearance of the target was randomly determined between 1 second (1,000 milliseconds (ms)) and 8 seconds (8,000 ms) in increments of 0.25 seconds (250 ms). Therefore, the subjects could not predict the appearance timing of the target, and needed to continuously pay attention to the screen.

In such a task (psychomotor vigilanve task (PVT)), a trial in which a time taken for a subject to press the button after the target is displayed (reaction time (RT)) is short is interpreted as a high task performance of the subject. That is, if there is a tendency that a RT for each trial is shorter as the variation amount of the pupil diameter of each subject calculated for each trial is smaller, it is indicated that the estimation device 10 can estimate, in real time, a task performance of a subject in a case where the gaze screen is dark.

Note that, in this task, immediately after a subject pressed the button, a RT taken to press the button was displayed for 1 second (1,000 ms), and the subject could confirm his/her RT for each trial.

Figure 5:
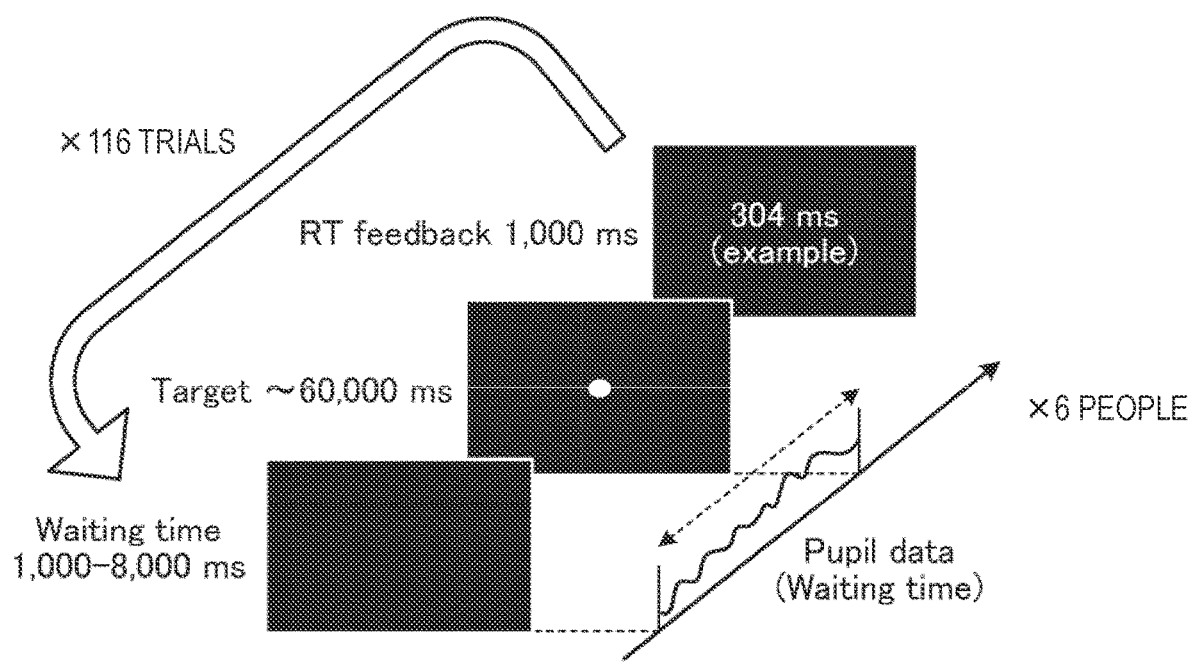
FIG. 5 is a diagram for describing a flow of an experiment.

In addition, data of a pupil diameter of a subject (pupil data) was measured during a waiting time from immediately after the start of a trial to the appearance of the target, and a variation amount of the pupil diameter of the subject for each trial was calculated from the measurement result. The flow of the experiment described above is as illustrated in FIG. 5.

[Calculation process of pupil diameter] Hereinafter, a process of calculating a variation amount of a pupil diameter of each subject in this experiment will be described.

First, the estimation device 10 measured the pupil diameter of the left eye of each subject at a frequency of 1,000 times per second by using a pupil diameter measurement device as an optical device.

Next, the estimation device 10 calculated a median value of the pupil diameter in the entire experiment for each subject, and regarded a section in which the pupil diameter is equal to or smaller than ½ of the median value as a section during blinking. In time-series data of the pupil diameter of each subject, the estimation device 10 set the section during blinking and sections for 0.2 seconds before and after the section as sections in which noise related to the blinking may be included, and excluded the sections as invalid data.

Next, the estimation device 10 set, as valid data, data obtained by excluding the invalid data from the time-series data of the pupil diameter of each subject, and smoothed the time-series data of the pupil diameter by applying a weight matrix called a Hanning window to the valid data. Note that the size of the Hanning window was 50 points.

Here, in a case where a continuous section of the valid data is short (for example, in a case where blinking occurs at a high frequency), there is a possibility that the estimation device 10 cannot appropriately perform the smoothing. Therefore, the estimation device 10 performed an operation of temporarily linearly interpolating the sections of the invalid data in the time-series data of the pupil diameter to perform the smoothing, and invalidating the linearly interpolated sections in the subsequent processing.

Next, the estimation device 10 calculated a variation amount of the pupil diameter by obtaining first-order differential values of the time-series data of the pupil diameter, taking absolute values of the obtained time-series data of the variation amount of the pupil diameter, and calculating the average of the obtained absolute values. Next, the estimation device 10 logarithmically transformed the calculated variation amount of the pupil diameter, and similarly logarithmically transformed a RT.

Finally, the estimation device 10 normalized, for each subject, the variation amounts of the pupil diameter and the RTs obtained by the above processing. Each normalized variation amount of the pupil diameter is referred to as a normalized pupil diameter variation amount (normalized amount of change in pupil data). In addition, each normalized RT is referred to as a normalized RT.

The estimation device 10 performed normalization called z-score in the above normalization. This z-score is obtained by subtracting the average value of values to be normalized from each of the values and then dividing the obtained value by the standard deviation of the values. According to this z-score, a large value is calculated in a case where a variation amount of a pupil diameter or a RT is relatively large for each individual subject, and a small value is calculated in a case where the variation amount of the pupil diameter or the RT is relatively small for each individual subject. As a result, the estimation device 10 can ignore individual differences of the subjects, such as a constant large or small variation amount of a pupil diameter and a constant large or small RT, and consider differences in the variation amounts of the pupil diameter and in the RTs that varied in real time for each individual subject executing the task.

[Experimental result] As a result of excluding invalid trials such as a trial in which a subject closed the eyes in a measurement section of the pupil diameter of the subject, the estimation device 10 obtained data of 687 variation amounts of the pupil diameters and 696 RTs by the above procedure.

Figure 6:
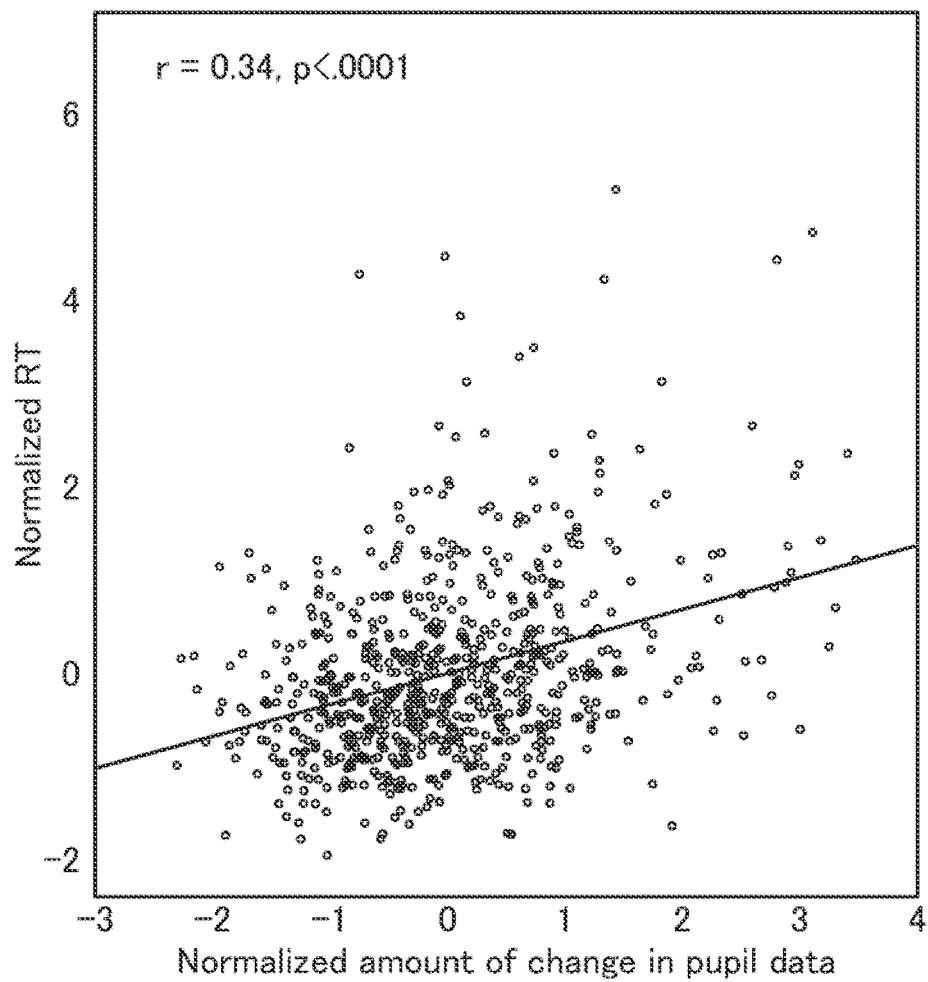
FIG. 6 is a diagram illustrating an experimental result.

Among the data, the obtained 687 variation amounts of the pupil diameters and the corresponding 687 RTs were used to show the relationship between the normalized amounts of change in pupil data and the normalized RTs, which is illustrated in a scatter diagram of FIG. 6. In this data, a correlation coefficient (Pearson's r) between the normalized amounts of change in pupil data and normalized RTs was examined and found to be 0.34, and as a result of performing a test called Permutation test, $p<0.0001$ was found to be significant.

That is, in each trial, it is shown that a RT increased as a variation amount of a pupil diameter increased. In other words, it is shown that there was a tendency that a RT for each trial was shorter as a variation amount of a pupil diameter calculated for each trial was smaller. This shows that, when the estimation device 10 acquires a variation amount of a pupil diameter of a subject executing a task in a case where a gaze screen of the subject is dark, the level of a task performance of the subject can be estimated in real time.

[System configuration and others] Furthermore, each component of each illustrated unit is functionally conceptual, and does not necessarily have to be physically configured as illustrated. That is, a specific form of distribution and integration of components of each device is not limited to the illustrated form. All or a part of the components may be functionally or physically distributed and integrated in any unit according to various loads, usage conditions, and the like. Furthermore, all or any part of processing functions performed in each device can be implemented by a CPU and a program executed by the CPU, or can be implemented as hardware by wired logic.

In addition, among the processing described in the embodiments, all or a part of processing described as being automatically performed may be manually performed, or all or a part of processing described as being manually performed may be automatically performed by a known method.

In addition, the processing procedure, the control procedure, the specific name, and the information including various types of data and parameters illustrated in the above document and the drawings can be arbitrarily changed unless otherwise specified.

[Program] The estimation device 10 can be implemented by a program as package software or online software being installed in a desired computer. For example, causing an information processing device to execute the above program makes it possible for the information processing device to function as the estimation device 10 in each of the embodiments. The information processing device mentioned here includes a desktop or notebook personal computer. Moreover, the information processing device also includes a mobile communication terminal such as a smartphone, a mobile phone, or a personal handyphone system (PHS), a terminal such as a personal digital assistant (PDA), and the like.

Furthermore, in a case where a terminal device used by a user is implemented as a client, the estimation device 10 can also be implemented as a server device that provides a service related to the above processing to the client. In this case, the server device may be implemented as a web server, or may be implemented as a cloud that provides a service related to the above processing by outsourcing.

Figure 7:
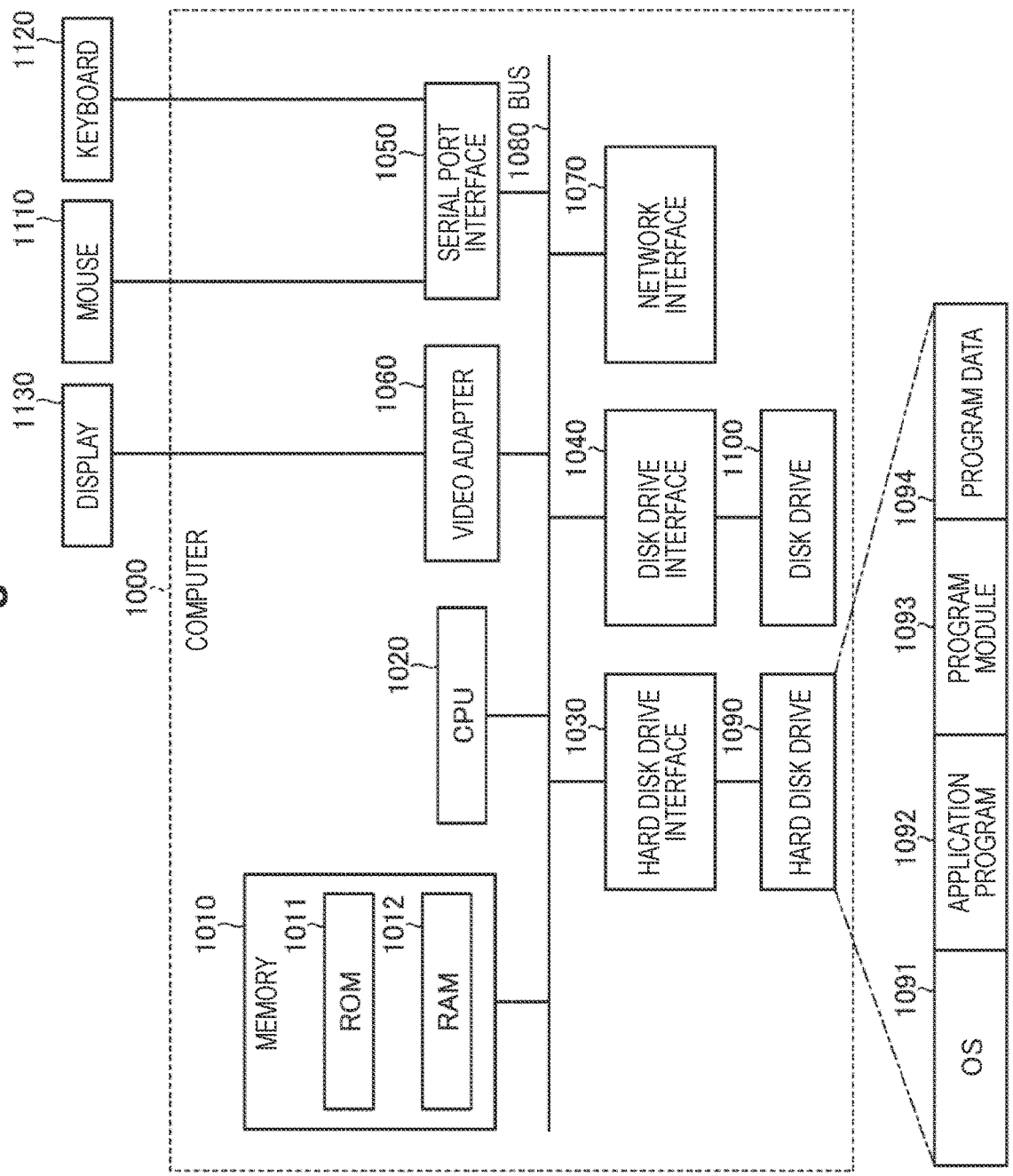
FIG. 7 is a diagram illustrating a configuration example of a computer that executes an estimation program.

FIG. 7 is a diagram illustrating an example of a computer that executes an estimation program. A computer 1000 includes, for example, a memory 1010 and a CPU 1020. Furthermore, the computer 1000 also includes a hard disk drive interface 1030, a disk drive interface 1040, a serial port interface 1050, a video adapter 1060, and a network interface 1070. These units are connected to each other by a bus 1080.

The memory 1010 includes a read only memory (ROM) 1011 and a random access memory (RAM) 1012. The ROM 1011 stores, for example, a boot program such as a basic input output system (BIOS). The hard disk drive interface 1030 is connected to a hard disk drive 1090. The disk drive interface 1040 is connected to a disk drive 1100. For example, a removable storage medium such as a magnetic disk or an optical disc is inserted into the disk drive 1100. The serial port interface 1050 is connected to, for example, a mouse 1110 and a keyboard 1120. The video adapter 1060 is connected to, for example, a display 1130.

The hard disk drive 1090 stores, for example, an OS 1091, an application program 1092, a program module 1093, and program data 1094. That is, a program that defines each processing executed by the estimation device 10 is implemented as the program module 1093 in which a code executable by a computer is described. The program module 1093 is stored in, for example, the hard disk drive 1090. For example, the program module 1093 for executing processing similar to the functional configurations in the estimation device 10 is stored in the hard disk drive 1090. Note that the hard disk drive 1090 may be replaced with an SSD.

Furthermore, data used in the processing in the above-described embodiments is stored as the program data 1094, for example, in the memory 1010 or the hard disk drive 1090. The CPU 1020 then reads the program module 1093 and the program data 1094 stored in the memory 1010 or the hard disk drive 1090 to the RAM 1012, and executes the program module 1093 and the program data 1094 as necessary.

Note that the program module 1093 and the program data 1094 are not limited to being stored in the hard disk drive 1090, and may be stored in, for example, a removable storage medium and read by the CPU 1020 via the disk drive 1100 or the like. Alternatively, the program module 1093 and the program data 1094 may be stored in another computer connected via a network (local area network (LAN), wide area network (WAN), or the like). The program module 1093 and the program data 1094 may be read by the CPU 1020 from the another computer via the network interface 1070.

REFERENCE SIGNS LIST

10 Estimation device
11 Input/output unit
12 Storage unit
13 Control unit
131 Data acquisition unit
132 Variation amount calculation unit
133 Determination unit
134 Estimation unit

The invention claimed is:

1. An estimation device comprising:
processing circuitry configured to:
acquire a pupil diameter of a subject whose work performance is to be estimated at a time of work and a luminance of a gaze target of the subject;
calculate a variation amount of the pupil diameter of the subject from time-series data of the pupil diameter of the subject;
determine whether or not the luminance of the gaze target of the subject is equal to or higher than a predetermined value; and
determine that a correlation between a magnitude of the variation amount of the pupil diameter of the subject and a deterioration in the work performance of the subject is low in a case where it is determined that the luminance of the gaze target of the subject is equal to or higher than a predetermined threshold, determine that the correlation between the magnitude of the variation amount of the pupil diameter of the subject and the deterioration in the work performance of the subject is high in a case where it is determined that the luminance of the gaze target of the subject is lower than the predetermined threshold, and estimate the work performance of the subject based on a result of the determination and the variation amount of the pupil diameter of the subject.

2. The estimation device according to claim 1, wherein the processing circuitry is further configured to estimate that the work performance of the subject is higher as the variation amount of the pupil diameter of the subject is larger in a case where it is determined that the luminance of the gaze target is equal to or higher than the predetermined threshold, and estimate that the work performance of the subject is lower as the variation amount of the pupil diameter of the subject is larger in a case where it is determined that the luminance of the gaze target is lower than the predetermined threshold.

3. The estimation device according to claim 1, wherein the processing circuitry is further configured to estimate that the work performance of the subject is lower as the variation amount of the pupil diameter of the subject is smaller in a case where it is determined that the luminance of the gaze target is equal to or higher than the predetermined threshold, and estimate that the work performance of the subject is higher as the variation amount of the pupil diameter of the subject is smaller in a case where it is determined that the luminance of the gaze target is lower than the predetermined threshold.

4. The estimation device according to claim 1, wherein the processing circuitry is further configured to exclude, from the time-series data of the pupil diameter of the subject, time-series data of the pupil diameter in a period in which a value of the pupil diameter is equal to or smaller than a predetermined threshold among the time-series data of the pupil diameter of the subject, and calculate the variation amount of the pupil diameter of the subject from the time-series data obtained by the exclusion.

5. The estimation device according to claim 1, wherein the processing circuitry is further configured to smooth the time-series data of the pupil diameter of the subject by use of a low-pass filter or a moving average to calculate the variation amount of the pupil diameter of the subject.

6. The estimation device according to claim 1, wherein the processing circuitry is further configured to obtain first-order differential values of the time-series data of the pupil diameter of the subject, takes take absolute values of the first-order differential values of the time-series data, calculate an average value of the absolute values of the first-order differential values of the time-series data, and calculate the variation amount of the pupil diameter of the subject by use of the calculated average value.

7. The estimation device according to claim 1, wherein the processing circuitry is further configured to set a value obtained by logarithmically transforming the calculated variation amount of the pupil diameter of the subject as the variation amount of the pupil diameter of the subject.

8. An estimation method executed by an estimation device, the estimation method comprising:
acquiring a pupil diameter of a subject whose work performance is to be estimated at a time of work and a luminance of a gaze target of the subject;
calculating a variation amount of the pupil diameter of the subject from time-series data of the pupil diameter of the subject;
determining whether or not the luminance of the gaze target of the subject is equal to or higher than a predetermined value; and
determining that a correlation between a magnitude of the variation amount of the pupil diameter of the subject and a deterioration in the work performance of the subject is low in a case where it is determined that the luminance of the gaze target of the subject is equal to or higher than a predetermined threshold, determining that the correlation between the magnitude of the variation amount of the pupil diameter of the subject and the deterioration in the work performance of the subject is high in a case where it is determined that the luminance of the gaze target of the subject is lower than the predetermined threshold, and estimating the work performance of the subject based on a result of the determination and the variation amount of the pupil diameter of the subject.

9. A non-transitory computer-readable recording medium storing therein an estimation program that causes a computer to execute a process comprising:

acquiring a pupil diameter of a subject whose work performance is to be estimated at a time of work and a luminance of a gaze target of the subject;

calculating a variation amount of the pupil diameter of the subject from time-series data of the pupil diameter of the subject;

determining whether or not the luminance of the gaze target of the subject is equal to or higher than a predetermined value; and determining that a correlation between a magnitude of the variation amount of the pupil diameter of the subject and a deterioration in the work performance of the subject is low in a case where it is determined that the luminance of the gaze target of the subject is equal to or higher than a predetermined threshold, determining that the correlation between the magnitude of the variation amount of the pupil diameter of the subject and the deterioration in the work performance of the subject is high in a case where it is determined that the luminance of the gaze target of the subject is lower than the predetermined threshold, and estimating the work performance of the subject based on a result of the determination and the variation amount of the pupil diameter of the subject.

* * * * *